United States Patent
Hsu et al.

(10) Patent No.: US 10,871,427 B2
(45) Date of Patent: Dec. 22, 2020

(54) BIOLOGICAL LIQUID COLLECTION VESSELS, SYSTEMS, AND METHODS

(71) Applicants: Alex Hsu, Edgewater, NJ (US); Scott Salmon, Tenafly, NJ (US); Radu Saftoiu, Landing, NJ (US)

(72) Inventors: Alex Hsu, Edgewater, NJ (US); Scott Salmon, Tenafly, NJ (US); Radu Saftoiu, Landing, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 264 days.

(21) Appl. No.: 14/418,844

(22) PCT Filed: Aug. 1, 2013

(86) PCT No.: PCT/US2013/053207
§ 371 (c)(1),
(2) Date: Jan. 30, 2015

(87) PCT Pub. No.: WO2014/022653
PCT Pub. Date: Feb. 6, 2014

(65) Prior Publication Data
US 2015/0211966 A1    Jul. 30, 2015

Related U.S. Application Data

(60) Provisional application No. 61/678,760, filed on Aug. 2, 2012.

(51) Int. Cl.
*B01L 3/00* (2006.01)
*G01N 1/34* (2006.01)
(Continued)

(52) U.S. Cl.
CPC ............... *G01N 1/34* (2013.01); *A61B 5/154* (2013.01); *A61B 5/150343* (2013.01);
(Continued)

(58) Field of Classification Search
CPC ............... G01N 1/34; A61B 5/150786; A61B 5/150755; A61B 5/150343; A61B 5/154;
(Continued)

(56) References Cited

U.S. PATENT DOCUMENTS

3,513,976 A * 5/1970 James ............... B01L 3/5021
210/361
3,741,400 A   6/1973 Dick
(Continued)

FOREIGN PATENT DOCUMENTS

| DE | 27 06 566 A1 | 8/1977 |
|---|---|---|
| EP | 0 508 530 A1 | 10/1992 |
| WO | 2008/143570 A1 | 11/2008 |

OTHER PUBLICATIONS

Extended EP Search Report dated Apr. 13, 2016 of corresponding European Application No. 13825273.9, 5 Pages.
(Continued)

*Primary Examiner* — Jill A Warden
*Assistant Examiner* — Dwayne K Handy (57) ABSTRACT

A biological liquid collection vessel is adapted to contain a biological liquid to be centrifuged. The collection vessel has a vessel body having an open upper end and a closed lower end, a continuous wall, a target area at the upper end, and a solids area at the lower end that is connected to the target area. The target area is extended in length. In some embodiments, a volume capacity of both of the target area and the solids area are configured so that a red blood cell portion of the centrifuged biological liquid (e.g., blood) is substantially contained in the solids area, and the serum or plasma portion of the centrifuged biological liquid is substantially contained in the target area. Methods of and systems using the liquid collection vessels are provided, as are other aspects.

27 Claims, 10 Drawing Sheets

(51) Int. Cl.
*A61B 5/154* (2006.01)
*A61B 5/15* (2006.01)
*A61B 5/153* (2006.01)

(52) U.S. Cl.
CPC .. *A61B 5/150755* (2013.01); *A61B 5/150786* (2013.01); *B01L 3/5021* (2013.01); *A61B 5/153* (2013.01); *A61B 5/15003* (2013.01); *A61B 5/150351* (2013.01); *B01L 2200/025* (2013.01); *B01L 2300/0854* (2013.01); *B01L 2300/0858* (2013.01)

(58) Field of Classification Search
CPC .......... A61B 5/15003; A61B 5/150351; A61B 5/153; B01L 3/5021; B01L 2200/025; B01L 2300/0854; B01L 2300/0858
See application file for complete search history.

(56) References Cited

U.S. PATENT DOCUMENTS

| | | | | |
|---|---|---|---|---|
| 3,750,645 A * | 8/1973 | Bennett | ........... | A61J 1/065 210/787 |
| 4,052,320 A | 10/1977 | Jakubowicz | | |
| 4,511,349 A * | 4/1985 | Nielsen | ........... | B01L 3/5021 422/533 |
| 4,534,863 A * | 8/1985 | Bacon | ........... | B01D 29/01 210/232 |
| 4,730,624 A * | 3/1988 | Waters | ........... | A61B 5/15003 600/577 |
| 4,861,477 A * | 8/1989 | Kimura | ........... | B01L 3/5021 210/359 |
| 5,422,018 A * | 6/1995 | Saunders | ........... | B01D 21/20 210/512.1 |
| 6,251,660 B1 | 6/2001 | Muir et al. | | |
| 6,612,997 B1 | 9/2003 | Hutton | | |
| 6,991,898 B2 | 1/2006 | O'Connor | | |
| 7,736,593 B2 | 6/2010 | Dastane et al. | | |
| 2005/0074363 A1 | 4/2005 | Dunfee | | |
| 2007/0161491 A1 * | 7/2007 | Jinno | ........... | B01L 3/5021 494/16 |
| 2010/0218621 A1 | 9/2010 | Chen et al. | | |
| 2011/0187021 A1 | 8/2011 | Losada et al. | | |

OTHER PUBLICATIONS

PCT International Search Report and Written Opinion dated Dec. 23, 2013 (11 Pages).

* cited by examiner

BIOLOGICAL LIQUID COLLECTION VESSELS, SYSTEMS, AND METHODS

FIELD

The present invention relates generally to vessels and methods adapted to collect biological liquid specimens.

BACKGROUND

In automated medical specimen testing, a volume of biological liquid specimen may be added to a biological liquid collection vessel. The collection vessel may then be centrifuged to separate the biological liquid specimen (e.g., blood) into its constituent parts, namely into the serum portion and red blood cell (RBC) portion. The serum portion lies atop the settled RBC portion. In some cases, there may also be a gelatinous layer adapted to help further separate and prevent remixing of the serum portion and the (RBC) portion. Once separated via centrifugation, a probe may be lowered by an automatic sampling system and some amount of the serum portion may be aspirated. The serum may be dispensed by the system into a testing vessel (e.g., cuvette) along with other components (e.g., a reagent and possibly a diluent) and may be tested to determine a presence of an analyte, other identifiable substance, or a characteristic of the serum. In some embodiments, only a relatively small amount of biological liquid specimen may be present in the collection vessel. This may be because previous sampling has already depleted the amount of serum portion that remains. In such instances, the remaining serum portion may be poured off into a smaller vessel, generally referred to as a micro-sampling container. This pour off of the remaining serum portion may cause spillage. In other cases, due to the health or age of the patient, collecting large samples may be contraindicated or challenging. Accordingly, apparatus, systems, and methods that may improve liquid handling for small-sized specimens are desired.

SUMMARY

According to a first aspect, a biological liquid collection vessel is provided. The biological liquid collection vessel includes a vessel body having an open end, a closed end, and a continuous inner wall extending from the open end to the closed end, the continuous inner wall being adapted to be in contact with a biological liquid and having an inner transverse dimension that varies along a length of the continuous inner wall, the inner transverse dimension having a minimum dimension located in between the open end and the closed end.

According to another aspect, a biological liquid collection vessel is provided. The biological liquid collection vessel includes a vessel body having an upper end and a lower end, a target area of a first average transverse dimension being open at the upper end and adapted to contain a serum portion, and a solids area connected to the target area having a second average transverse dimension larger than the first average transverse dimension, being closed at the lower end and adapted to contain a red blood cell portion.

According to another yet aspect, a biological liquid collection vessel adapted to contain a centrifuged biological liquid is provided. The biological liquid collection vessel includes a vessel body having an upper end and a lower end, a target area being open at the upper end, and a solids area connected to the target area and being closed at the lower end, and wherein volume capacities of both of the target area and the solids area are configured and adapted so that a red blood cell portion of the centrifuged biological liquid is substantially contained in the solids area, and the serum or plasma portion of the centrifuged biological liquid is substantially contained in the target area. In a system aspect, a liquid aspiration system is provided. The liquid aspiration system includes a biological liquid collection vessel having a target area of a first average transverse dimension and being open at an upper end and containing substantially a serum or plasma portion, and a solids area connected to the target area having a second average transverse dimension larger than the first average transverse dimension and a closed bottom end, the solids area containing substantially a red blood cell portion, and a probe received in the biological liquid collection vessel and adapted to aspirate at least some of the serum or plasma portion from the target area. In a method aspect, an improved liquid centrifugation method is provided. The method includes providing a biological liquid collection vessel having a target area of a first average transverse dimension, being open at an upper end, and a solids area connected to the target area having a second average transverse dimension larger than the first transverse dimension and a closed bottom end, the solids area and the target area containing blood, and centrifuging the biological liquid collection vessel containing blood to separate the blood into a serum or plasma portion and a red blood cell portion, wherein the target area contains substantially the serum or plasma portion, and the solids area contains substantially the red blood cell portion.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

In current blood collection tubes, centrifugation of the blood may take place to separate the serum or plasma portion from the red blood cell portion. However, because the collection tubes are of a constant inner diameter, the area where the serum or plasma portion settles is generally very short. As such, only a limited height target area where the probe tip may aspirate the serum or plasma portion is provided in such conventional blood collection tubes.

Accordingly, in one aspect, an improved biological liquid collection vessel is provided that has an enlarged (e.g., longer) target area which is adapted to be accessed by a probe. The biological liquid collection vessel includes a vessel body having an open end, a closed end, and a continuous inner wall extending from the open end to the closed end. The continuous inner wall is adapted to be in contact with a biological liquid and has an inner transverse dimension dT that varies along a length of the inner wall. The inner transverse dimension dT has a minimum dimension located in between the open end and the closed end.

In some embodiments, the biological liquid collection vessel includes a vessel body having an upper and lower end, a target area of a first average transverse dimension that is adapted to contain a liquid portion (e.g., a serum or plasma portion), and a solids area connected to the target area having a second average transverse dimension larger than the first average transverse dimension that is adapted to contain a solids portion (e.g., a red blood cell portion). Volume capacities of the target area and solids area may be configured (e.g., sized) so that a centrifuged biological liquid (e.g., blood) when contained in the biological liquid collection vessel, has a red blood cell portion that is substantially contained in the solids area, and a serum or plasma portion that is substantially contained in the target area. Some embodiments include a multi-component body having, for example, an outer sleeve and an inner liner. Thus, micro-sampling capacity (e.g., less than or equal to about 3 mL) may be provided by the inner liner in a biological liquid collection vessel that is of a non-micro size (e.g., a 16 mm×100 mm tube). Thus, such biological liquid collection vessels may be received in standard-sized racks and equipment receptacles, yet provide micro-sized collection capacities. Moreover, the pour off of the serum or plasma portion prevalent in the prior art may be reduced or eliminated. These and other aspects and features of the invention will be described with reference to FIGS. 1A-9 herein.

Figures 1A, 1B, 1C:
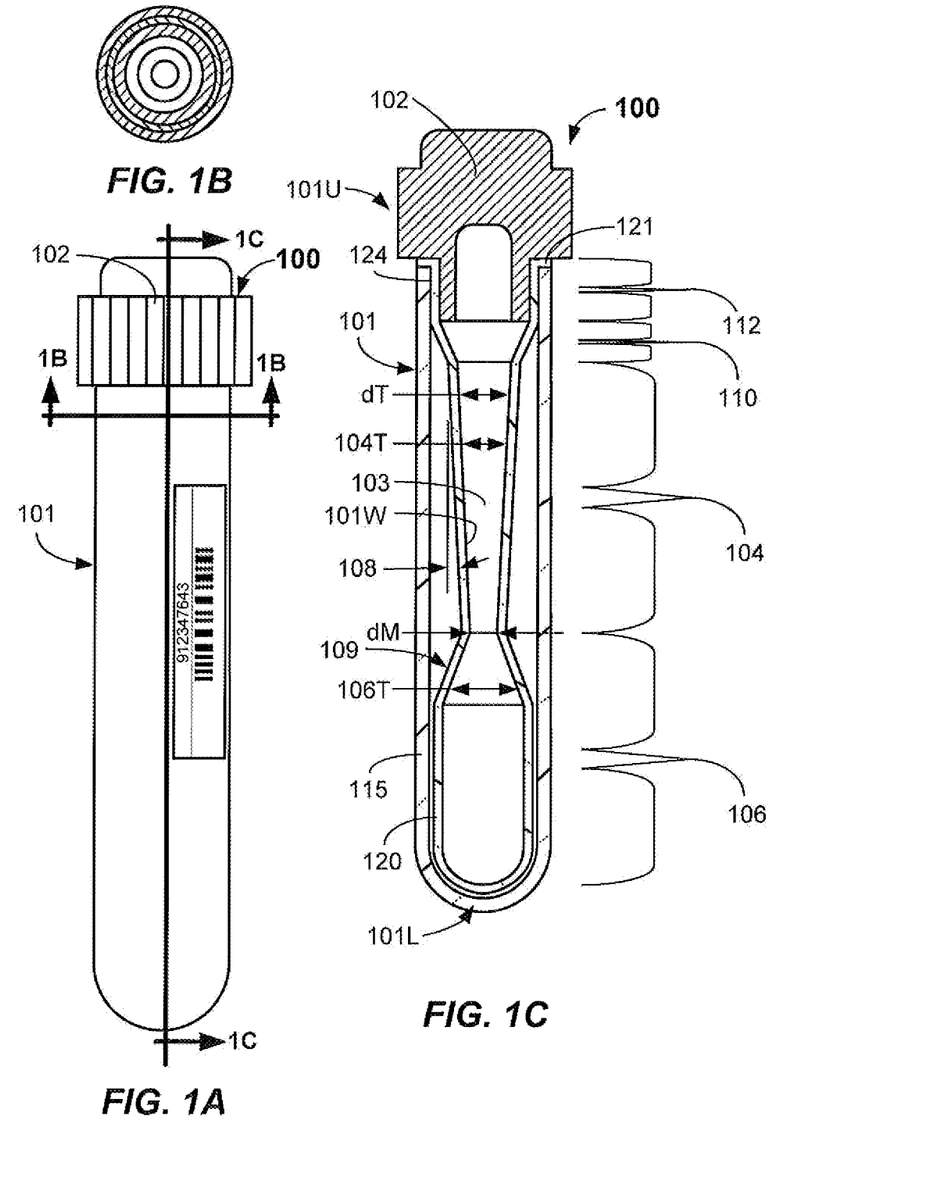
FIG. 1A illustrates a side plan view of a biological liquid collection vessel according to embodiments.
FIG. 1B illustrates a cross-sectioned end view of a biological liquid collection vessel taken along section line 1B-1B of FIG. 1A according to embodiments.
FIG. 1C illustrates a cross-sectioned side view of a biological liquid collection vessel taken along section line 1C-1C of FIG. 1A according to embodiments.

In accordance with a first embodiment of the invention, as best shown in FIGS. 1A-1C, a biological liquid collection vessel 100 is described. The biological liquid collection vessel 100 includes a vessel body 101 having an upper end 101U that is open and a lower end 101L (See FIG. 1C) that is closed. A cap 102 may be received in the upper end 101U and may be used to seal the vessel body 101. A suitable vacuum may be provided within a biological liquid receiving cavity 103 of the biological liquid collection vessel 100 to allow collection of a biological liquid (e.g. blood). The biological liquid collection vessel 100 further includes a continuous inner wall 101W of the vessel body 101 extending from the open upper end 101U to the closed lower end 101L. The continuous wall 101W may be generally constant thickness along a length thereof. The continuous inner wall 101W is adapted to be in contact with a biological liquid along its length, and has an inner transverse dimension dT (e.g., a diameter) that varies along a length of the continuous inner wall 101W. In embodiments, the inner transverse dimension dT has a minimum dimension dM located in between the open upper end 101U and the closed lower end 101L.

The biological liquid collection vessel 100 further includes a target area 104 above the minimum dimension dM having a first average transverse dimension 104T. The target area 104 is open at the upper end 101U so that it may be accessed by a probe 870 (FIGS. 8A-8B), and is adapted to contain substantially a liquid portion 855 after centrifugation (e.g., a serum or plasma portion). The biological liquid collection vessel 100 further includes a solids area 106 connected to the target area 104 having a second average transverse dimension 106T that may be larger than the first average transverse dimension 104T in some embodiments. The solids area 106 is closed at the lower end 101L and adapted to substantially contain a solids portion 860 (FIG. 8A) after centrifugation (e.g., a red blood cell portion).

In one or more embodiments of the biological liquid collection vessel 100, the solids area 106 and the target area 104 are adapted to contain a total volume of a biological liquid, and wherein a volume of the solids area 106 may be sized to be between about 40% to 80% of the total volume, or even between about 50% to 70% of the total volume in some embodiments. In one or more embodiments, the solids area 106 and the target area 104 are adapted to contain a total volume, and a volume of the target area 104 may be sized to be between about 20% to about 60% of the total volume, or even between about 30% to about 50% of the total volume in some embodiments. In one or more embodiments, the target area 104 may include a larger dimension at an upper end and a smaller dimension dM at the lower end of the target area 104. In one embodiment, an inner taper (e.g., a funnel shape) may be formed along a substantial portion of a length of the target area 104. The inner taper may have a wider dimension (e.g., diameter) adjacent to the upper end 101U. The inner taper may have a linear taper angle 108 of between about 0.25 degrees to about 30 degrees, or even 0.25 degrees to about 15 degrees. In other embodiments, the taper may be non-linear along its length, i.e., the taper can be radiused or made up of interconnected conical regions having different cone angles.

As shown in FIG. 1C, a reverse taper 109 may be formed along an upper portion of the solids area 106 wherein the reverse taper 109 has a smaller portion adjacent to the target area 104, i.e., at the location of the minimum dimension dM. In the depicted embodiment, the target area 104 and the solids area 106 may meet and form the minimum diameter dM. For example, in the depicted embodiment, the inner taper of the target area 104 and the reverse taper 109 of the solids area 106 may meet and form the minimum diameter dM. The location of the minimum diameter dM may vary along a height of the vessel 100, but may be selected based upon the expected distribution between serum or plasma portion and the RBC portion after centrifugation of the blood from a healthy patient. However, to be clear, the location of dM may not always coincide with the location of the line of demarcation (e.g., boundary) between the serum or plasma portion and the RBC portion after centrifugation, as the degree of hydration, heath, and age of the patient may allow the ratios between the serum and plasma portions and RBC portions to vary somewhat. Thus, the location of the minimum dimension dM may be varied in height location to achieve different volume ratios for the serum or plasma area 104 and the solids area 106, even if they do not match the anticipated separation ratios of RBC and serum. In other words, the line of demarcation (e.g., boundary) between the serum or plasma area 104 and the solids area 106 does not need to exactly coincide with the boundary between RBC portion and the serum or plasma portion. By adjusting these variables, one can optimize the target area 104 using various dimensions and volume proportions.

In one or more embodiments, the biological liquid collection vessel 100 may include a transition portion 110 that may have a generally larger average dimension (e.g., diameter) than the target area 104. The transition portion 110 is an area that may allow the phlebotomist to draw some small amount of extra blood, or simply allow a smooth transition to a cap-receiving portion 112. The transition portion 110 may be eliminated in some embodiments. The biological liquid collection vessel 100 may include a cap-receiving portion 112 that may generally include a cylindrical portion that is configured and adapted to receive the cap 102 and secure and seal the cap 102 therein. The cap-receiving portion 112 may be located above the transition portion 110, if present.

In one or more embodiments, the biological liquid collection vessel 100 may have a total volume capacity in the solids area 106 plus the target area 104 of less than or equal to 3 mL, or even less than or equal to 2 mL in some embodiments, or even less than or equal to 1.5 mL in some embodiments. Thus, the biological liquid collection vessel 100 may be considered a micro-sampling vessel in these embodiments.

In another aspect, the biological liquid collection vessel 100 may comprise a multi-piece construction. For example, the biological liquid collection vessel 100 may have an outer sleeve 115 and an inner liner 120. The inner liner 120 may have the target area 104 formed therein, as well as a portion of, or all of, the solids area 106. As shown in FIG. 1C, the inner liner 120 may be inserted inside of the outer sleeve 115. Vertical positioning of the inner liner 120 within the outer sleeve 115 may be controlled by a lip 121 on a top of the inner liner 120, whereas axial positioning may be controlled by a pilot 124 on the inner liner 120 registering on an inside surface of the outer sleeve 115. The outer sleeve 115 and inner liner 120 may be made from a generally clear (e.g., transparent, translucent, or opaque) material, such as a suitable plastic. A plastic material such as polyethylene, polypropylene, polyethylene terephthalate (PET), or the like, may be used in some embodiments. Optionally, the material may be a glass material. Other suitable materials may be used. The outer sleeve 115 and inner liner 120 may be connected by a suitable interference fit, adhesive, ultrasonic welding, or other suitable fastening means.

It should be recognized that the biological liquid collection vessel 100 according to one or more embodiments of the invention may have a collection capacity which is provided in the class of a micro-sampling vessel, yet the overall size of the biological liquid collection vessel 100 is the same as a standard collection vessel. For example, the outer sleeve 115 may comprise a first volume capacity V1, (without the inner sleeve 102) and the inner liner 120 may comprise a second volume capacity V2, and the ratio of V2/V1 may be less than about 0.167 to about 0.8. In this manner, micro-sampling capability is provided, yet the outside dimensions of the biological liquid collection vessel 100 are such that the biological liquid collection vessel 100 is compatible with standard sample racks and/or processing equipment, such as centrifuges and other clinical analysis instruments. Thus, the biological liquid collection vessel 100 may be used universally and retrofitted into existing systems. Examples of the relative capacities and sizes of embodiments of the biological liquid collection vessel 100 are shown in Table 1 below.

TABLE 1

Tube Dimensions and Collection Capacities

Figures 6A, 6B, 6C, 6D:
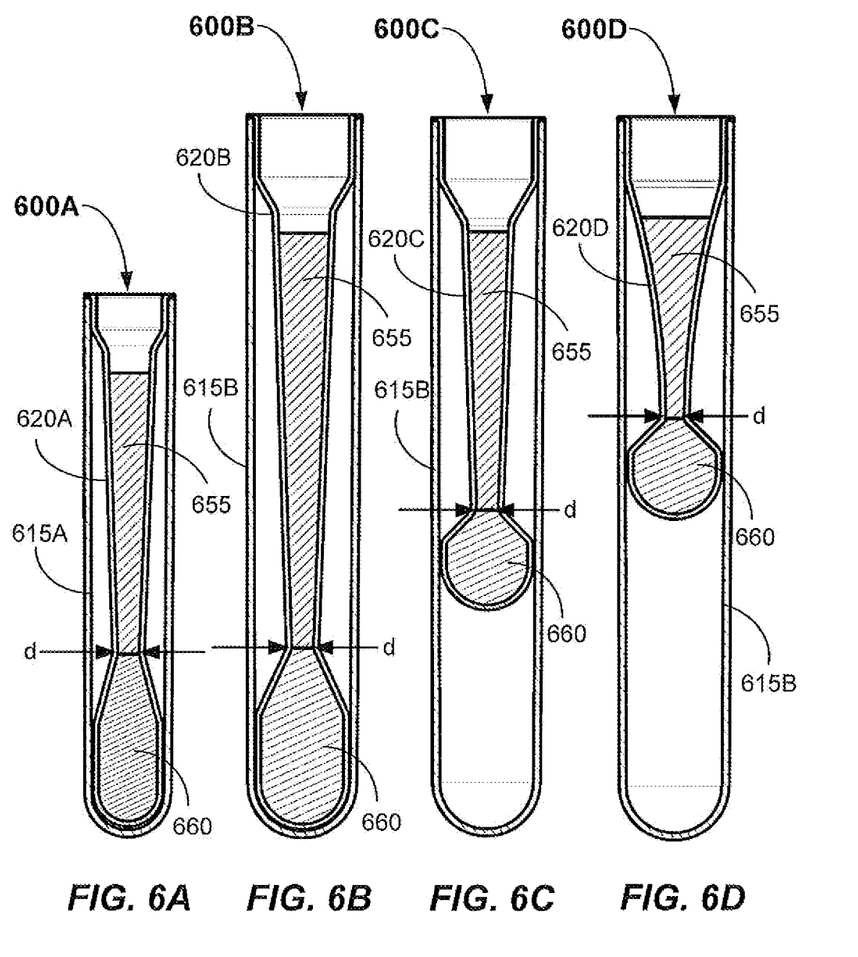
FIGS. 6A-6F illustrates cross-sectioned side views of alternative biological liquid collection vessel including serum or plasma portion and red blood cell portions according to embodiments.
Figure 6E:
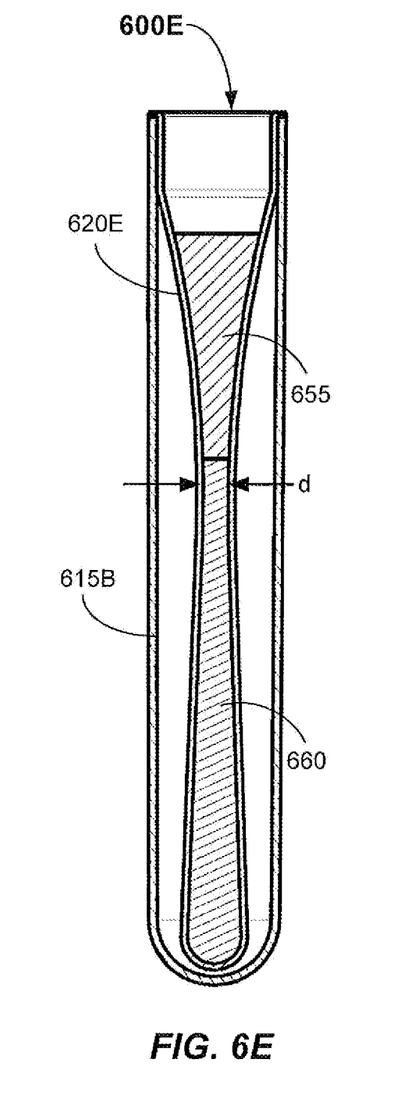
Figure 6F:
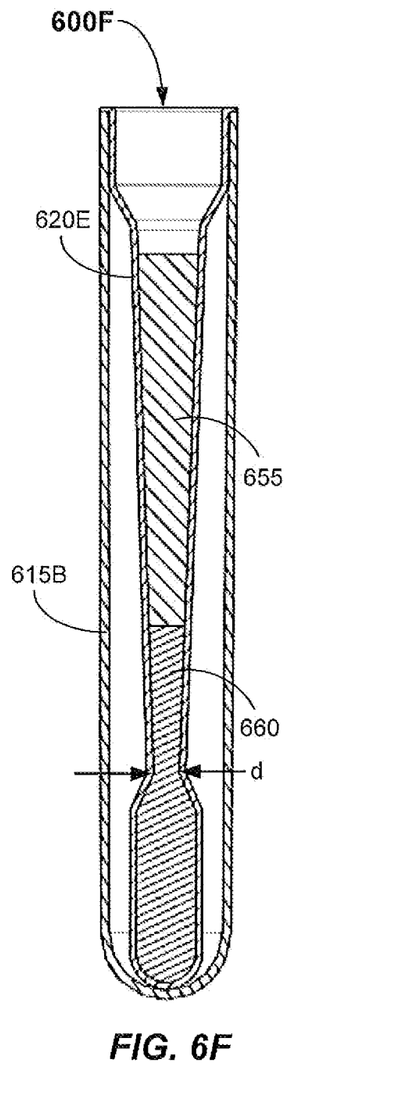

| Tube | Size | V1 | V2 | Serum or Plasma volume | RBC Volume | Ratio %/% |
|---|---|---|---|---|---|---|
| FIG. 6A | 12.75 × 75 | 3 ml | 1.6 ml | 0.6 ml | 1.05 ml | 40/60 |
| FIG. 6B | 16 × 100 | 5 ml | 3.0 ml | 1.2 ml | 1.8 ml | 40/60 |
| FIG. 6C | 16 × 100 | 5 ml | 1.5 ml | 0.6 ml | 0.9 ml | 40/60 |
| FIG. 6D | 16 × 100 | 5 ml | 1.5 ml | 0.6 ml | 0.9 ml | 40/60 |
| FIG. 6E | 16 × 100 | 5 ml | 1.5 ml | 0.6 ml | 0.9 ml | 40/60 |

Figure 8A:
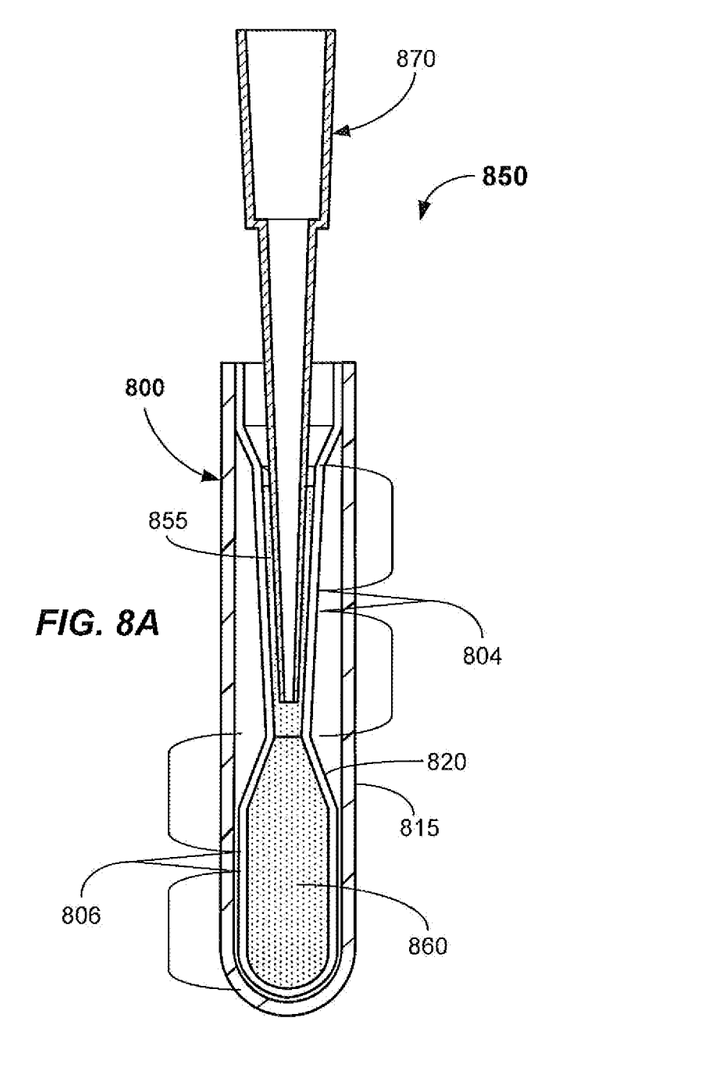
FIG. 8A illustrates a cross-sectioned side view of a probe inserted into a target area of a biological liquid collection vessel according to embodiments.

Thus, as shown in FIG. 8A, it should be understood that the volume capacities of the target area 804 and the solids area 806 may be appropriately sized so that a centrifuged biological liquid (e.g., blood) having a serum or plasma portion 855 and a red blood cell portion 860, when contained in the biological liquid collection vessel 100, results in the red blood cell portion 860 being substantially contained in the solids area 806, and the serum or plasma portion 855 being substantially contained in the target area 804. In the depicted embodiment, a line of demarcation between the red blood cell portion 860 and the serum or plasma portion 855 may be located approximately at the location of the minimum dimension d (FIG. 1C). If a gelatinous layer is used, the gelatinous layer will settle following centrifugation adjacent to the minimum dimension d with the serum or plasma portion 855 above, and the red blood cell portion 860 below.

Figures 2A, 2B, 3A, 3B:
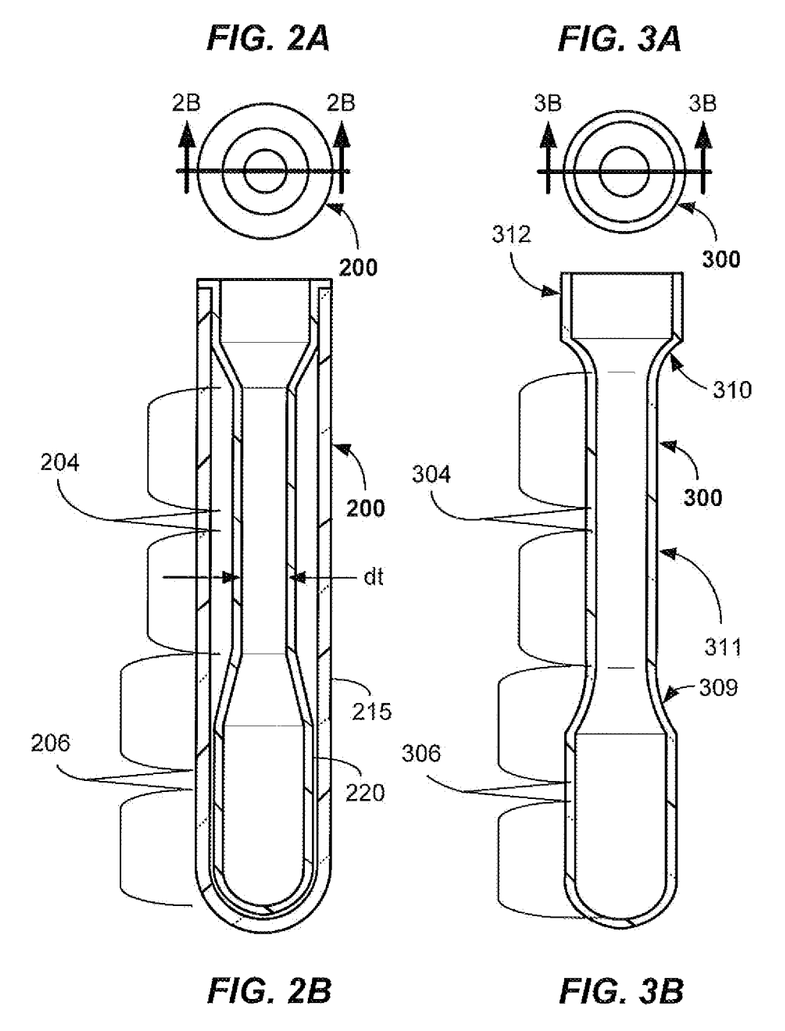
FIG. 2A illustrates a top view of an alternative biological liquid collection vessel according to embodiments.
FIG. 2B illustrates a cross-sectioned side view of the biological liquid collection vessel of FIG. 2A taken along section line 2B-2B according to embodiments.
FIG. 3A illustrates a top view of an alternative biological liquid collection vessel according to embodiments.
FIG. 3B illustrates a cross-sectioned side view of the biological liquid collection vessel of FIG. 3A taken along section line 3B-3B according to embodiments.

FIGS. 2A and 2B illustrate a first alternative embodiment of the biological liquid collection vessel 200. The construction of this embodiment of the biological liquid collection vessel 200 is the same as the FIGS. 1A-1C embodiment, having an inner liner 220 inserted into an outer sleeve 215.

However, the target area 204 in this embodiment has a substantially constant dimension dt along a length thereof, i.e., it is devoid of a taper, albeit the average transverse dimension of the target area 204 is less than an average transverse dimension of the solids area 206. As in the previous embodiment, having a reduced dimension in the target area 204 extends a length of the target area 204 so that a probe placement does not need to be so exacting and allows a larger percentage of the serum or plasma portion to be aspirated.

FIGS. 3A and 3B illustrate another alternative embodiment of the biological liquid collection vessel 300. The construction of this embodiment of the biological liquid collection vessel 300 is similar to the FIGS. 2A-2B embodiment, except that the biological liquid collection vessel 300 does not include an outer sleeve. The outer surface of the biological liquid collection vessel 300 includes an outer necked-down area 311 generally corresponding to a location of the target area 304. However, the cap-receiving portion 312 remains larger to accept a common-sized cap (not shown), and the solids area 306 is also of a size that it may be accepted into a standard-sized sample container rack or centrifuge receptacle. For example, in some embodiments, the outer diameter of the solids region 306 may be between about mm and 16 mm, i.e., the same diameter as a standard conventional blood collection tube. Furthermore, the overfill region 310 and reverse taper 309 of the solids region 306 may include non-linear tapers (e.g., may be radiused—as shown).

Figure 4A:
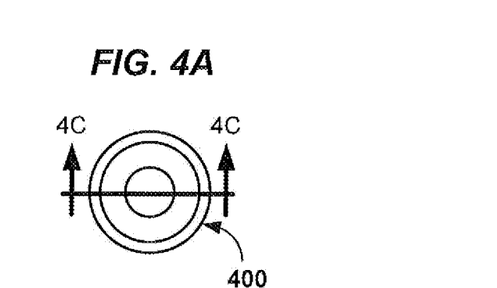
FIG. 4A illustrates a top view of an alternative biological liquid collection vessel according to embodiments.
Figures 4B, 4C:
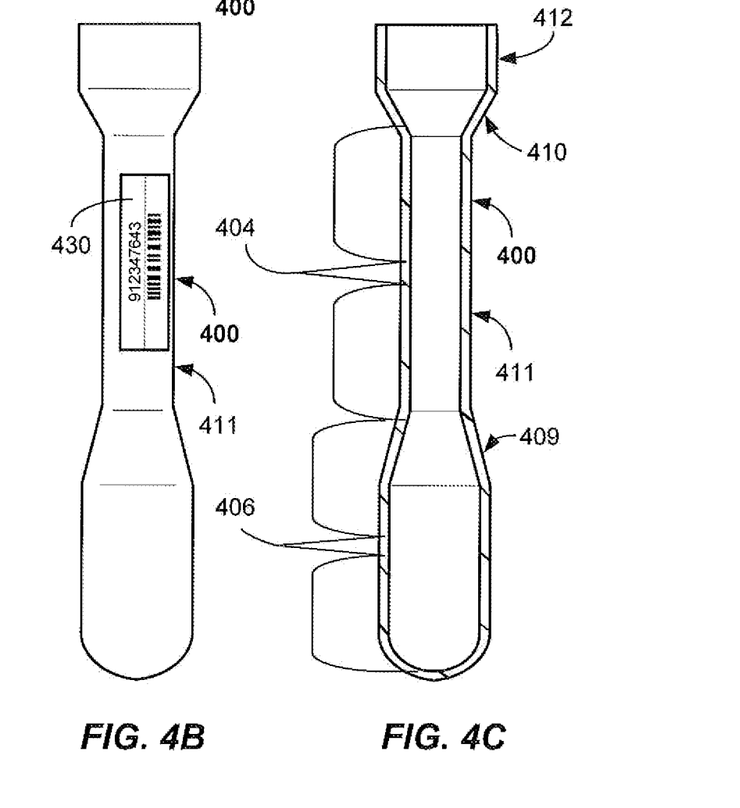
FIG. 4B illustrates a side plan view of the biological liquid collection vessel of FIG. 3A including a barcode label.
FIG. 4C illustrates a cross-sectioned side view of the biological liquid collection vessel of FIG. 4A taken along section line 4C-4C according to embodiments.
Figures 5A, 5B, 5C:
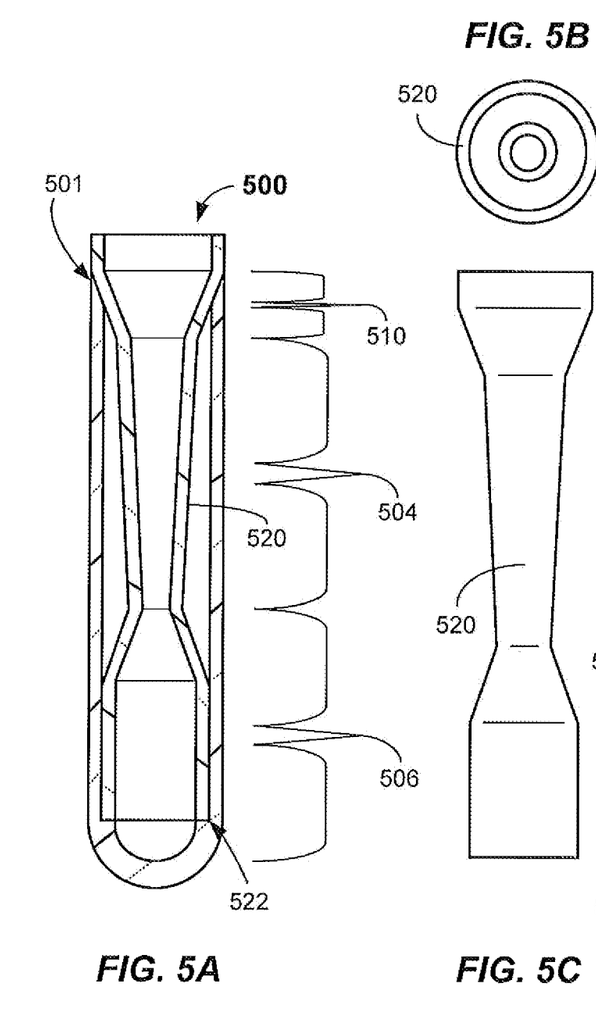
FIG. 5A illustrates a cross-sectioned side view of an alternative biological liquid collection vessel according to embodiments.
FIG. 5B illustrates an end plan view of an inner liner of the biological liquid collection vessel of FIG. 5A.
FIG. 5C illustrates a side plan view of the inner liner according to embodiments.
Figure 5D:
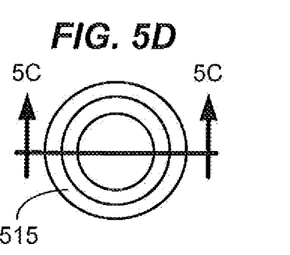
FIG. 5D illustrates an end plan view of an outer sleeve of the biological liquid collection vessel of FIG. 5A.
Figure 5E:
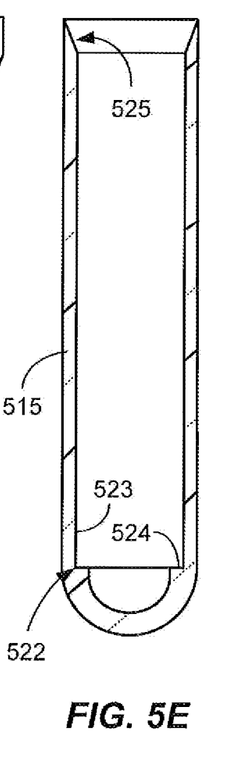
FIG. 5E illustrates a cross-sectioned side view of the outer sleeve according to embodiments.

FIGS. 4A-4C illustrate another alternative embodiment of the biological liquid collection vessel 400. The construction of this embodiment of the biological liquid collection vessel 400 is similar to the FIGS. 3A-3B embodiment, in that the biological liquid collection vessel 200 does not include an outer sleeve, i.e., it is of a one-piece construction. The outer surface of the biological liquid collection vessel 400 includes a necked-down area 411 generally corresponding to the location of the target area 404. The outer diameter of the solids region 406 and the cap-receiving region 412 may be between about 13 mm and 16 mm, i.e., the same diameter as standard conventional blood collection tubes. Furthermore, the overfill region 410 and reverse taper 409 of the solids region 406 may include linear tapers (as shown). A barcode label 430 may be applied at the necked-down area 411.

FIG. 5A-5E illustrates yet another alternative embodiment of the biological liquid collection vessel 500. The construction of this embodiment of the biological liquid collection vessel 500 is similar to the FIGS. 2A-2B embodiment, in that the biological liquid collection vessel 500 includes a vessel body 501 having an outer sleeve 515 and an inner liner 520, i.e., it has a multi-piece construction. However, in this embodiment, the bottom end of the inner liner 520 is open. The open bottom end registers in a registry surface 522 formed in the outer sleeve 515. The registry surface 522 may include a cylindrical portion 523 and/or an abutment 524 that contacts a lower end of the inner liner 520. The target area 504 is formed in the upper portion of the inner liner 520, and may include a taper. The solids area 506 is formed by the interaction of the inner liner 520 and the outer sleeve 515. The intersection thereof may be sealed by suitable adhesive, ultrasonic welding, or the like. The upper end of the outer sleeve 515 may include a tapered registry surface 525 that is received against the taper outside wall of the overfill portion 510. This intersection may be sealed such as by a suitable adhesive, ultrasonic welding, or the like.

FIGS. 6A-6F illustrate several other alternative embodiments of biological liquid collection vessels 600A-600F. The construction of these embodiments of the biological liquid collection vessels 600A-600F are similar to the FIGS. 2A-2B embodiment, in that the biological liquid collection vessels 600A-600F include an outer sleeve 615A, 615B and an inner liner 620A-620F inserted therein, i.e., each has a multi-piece construction. As can be seen, a volume-containing capacity of each of the biological liquid collection vessels 600A-600F may be varied by using different sized inner liners 620A-620F. For example, each outer sleeve 615A, 615B may have a first volume capacity V1, and the inner liner 620A-620F provided (e.g., inserted) therein may have a second volume capacity V2. Accordingly, in some embodiments, V2 is less than V1. For example, a ratio of V2/V1 may be less than about 0.8. Other ratios of V2/V1 may be used. In this manner, the biological liquid collection vessels 600A-600F may have outer dimensions that approximate standard blood collection tube dimensions, yet exhibit micro-scale collection capabilities. In each of the vessels 600A-600F, a centrifuged blood sample is provided with the serum or plasma portion 655 and a red blood portion 660. In some embodiments, the serum or plasma portion 655 is contained substantially in the target area, and the red blood portion 660 contained substantially in the solids area. In each of the embodiments shown, an inner transverse dimension dT of the inner liner 620A-620F varies along a length thereof. In one or more embodiments, the minimum dimension dM may be located at a transition location between the target area and the solids area. In each of the embodiments shown in FIGS. 6A-6F, the target area is extended in length as compared to a length of the target area would be in a standard-sized collection tube of the same diameter as the outer sleeve 615A, 615B.

Figure 7A:
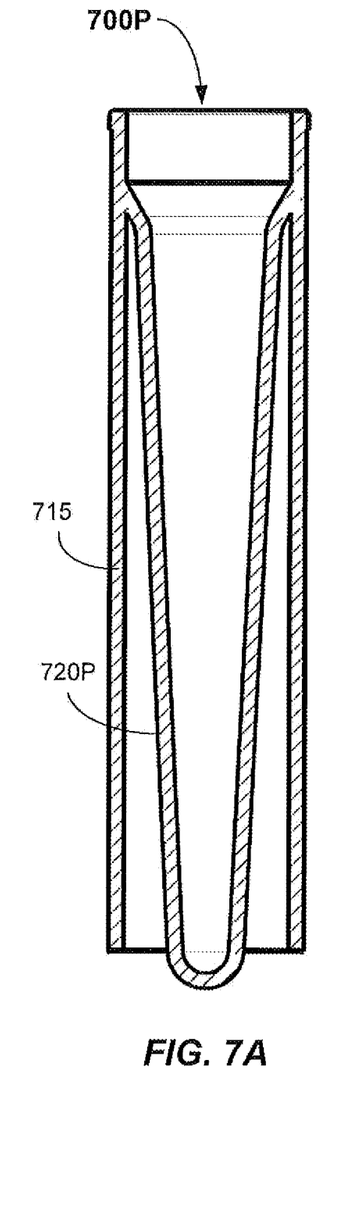
FIG. 7A illustrates a cross-sectioned side view of a preform adapted to form an alternative embodiment of biological liquid collection vessel according to embodiments.
Figure 7B:
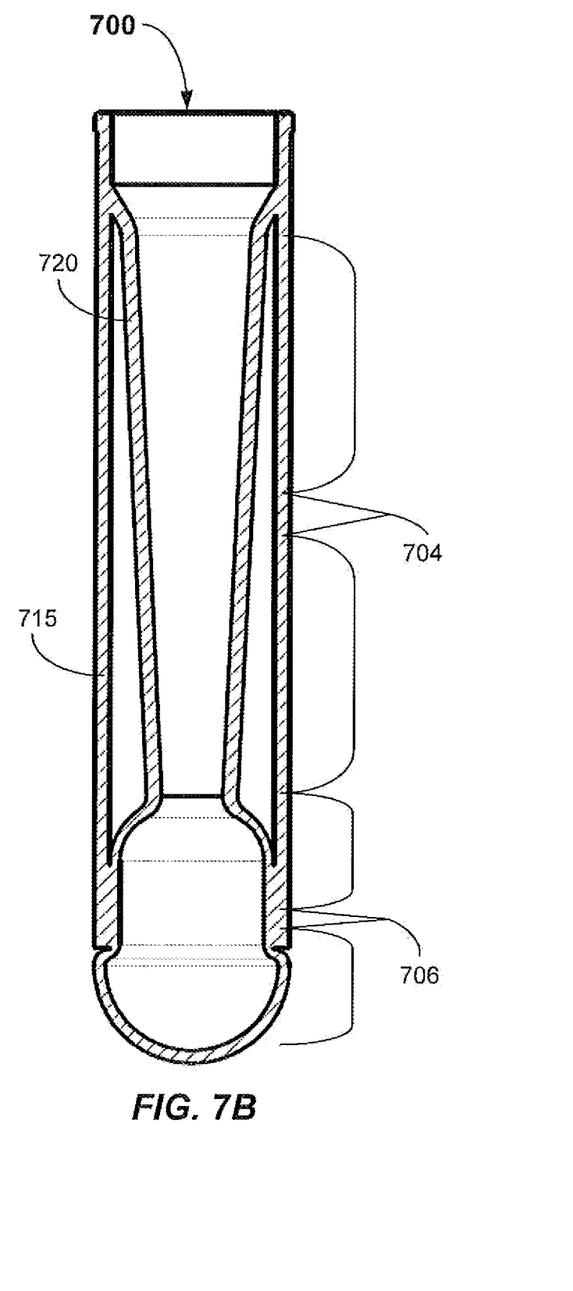
FIG. 7B illustrates a cross-sectioned side view of an alternative embodiment of biological liquid collection vessel according to embodiments.

FIGS. 7A-7B illustrate another alternative embodiment of a biological liquid collection vessel 700. The construction of this embodiment of the biological liquid collection vessel 700 is similar to the FIGS. 2A-2B embodiment, in that the biological liquid collection vessel 700 includes an outer sleeve 715 and an inner liner 720. However, in this embodiment, the biological liquid collection vessels 700 is formed from a preform 700P, as best shown in FIG. 7A. The preform 700P may be injection molded and may include an outer sleeve 715 similar to the previously-described embodiments, except that the sleeve 715 may include an open bottom. The preform 700P may also include an inner-sleeve forming portion 720P that may have any suitable shape, such as the tapered cone shape shown. To form the solids area 706 and the target area 704, the preform 700P may be inserted into a mold and the lower end of the inner-sleeve forming portion 720P may be locally heated to a suitable temperature to plasticize the lower end only by a suitable heater. Pressure may then be applied to the inside of the preform 700P and the heated lower portion may expand to the inside of the outer sleeve 715 and to the walls of the mold forming the configuration of the solids area 706.

Figure 8B:
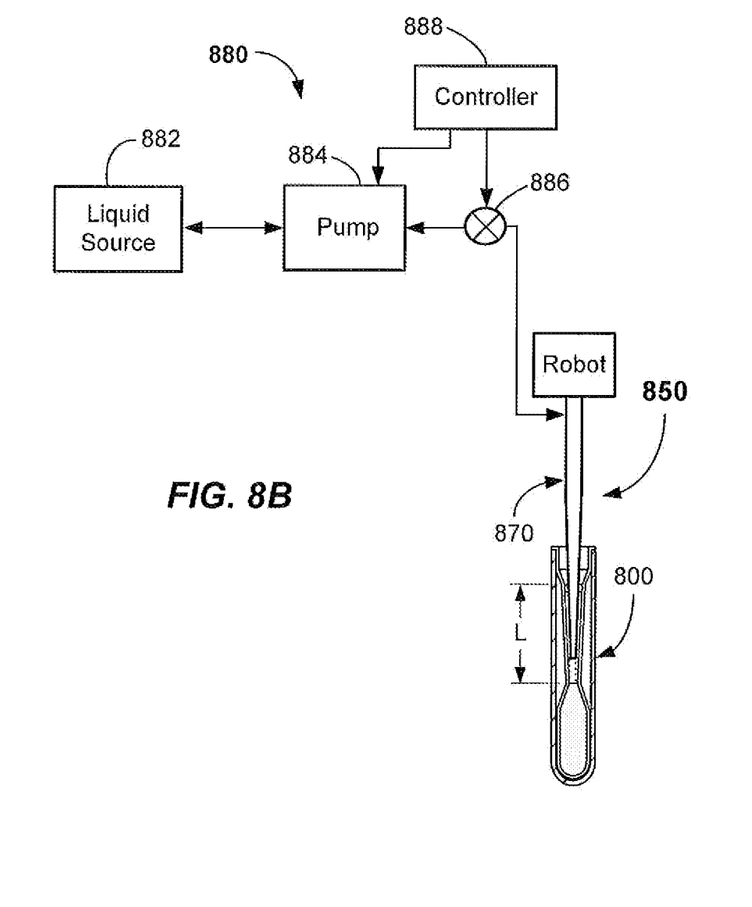
FIG. 8B illustrates a block diagram view of a liquid aspiration system according to embodiments.

FIGS. 8A-8B illustrate another alternative embodiment of the biological liquid collection vessel 800. The construction of this embodiment of the biological liquid collection vessel 800 is similar to the FIGS. 2A-2B embodiment, in that the biological liquid collection vessel 800 includes an outer sleeve 815 and an inner liner 820, i.e., it is of a two-piece construction as shown. However, other constructions of biological liquid collection vessels as described herein may be used. The target area 804 located at the top of the vessel 800 is adapted to receive a probe 870. The outer surface of the inner liner 820 and the inner surface of the outer sleeve 815, at least at the respective top ends thereof, may be adhered through the use of adhesive, ultrasonic welding, interference fit, or the like. The outer diameter of the outer sleeve 815 may be between about 10 mm and about 20 mm, or even between about 12 mm and about 18 mm, i.e., approximately the same diameter as a standard conventional blood collection tube. The biological liquid collection vessel 800 is shown containing a centrifuged biological liquid (e.g., centrifuged blood sample) having a liquid portion 855 (e.g., a serum or plasma portion) contained substantially within the target area 804 and a solids portion 860 (e.g., a red blood cell portion) contained substantially in the solids area 806. The actual location of the line of demarcation (e.g., the boundary) between the liquid portion 855 (e.g., serum or plasma portion) and solids portion 860 (e.g., red blood cell portion) will vary based upon the health, age, and/or condition of the patient.

In some cases where there is a higher percentage of the red blood cell portion 860 the line of demarcation may be slightly above the minimum dimension dM (see FIG. 1C), and where there is a lower percentage of the red blood cell portion 860, the line of demarcation may be slightly below the minimum dimension dM. However, the location is designed such that after centrifugation, the liquid portion 855 (e.g., a serum or plasma portion) is contained substantially within the target area 804 and a solids portion 860 (e.g., a red blood cell portion) is contained substantially in the solids area 806. The terms "contained substantially within" as used herein means that the respective target area 804 may include at least 60% of serum or plasma portion 855, and the solids area 860 may contain at least 60% solids portion 860 (e.g., a red blood cell portion).

FIGS. 8A-8B also illustrate a liquid aspiration system 850 including the biological liquid collection vessel 800 having a target area 804 of a first average transverse dimension and being open at an upper end and containing substantially the liquid portion 855 (e.g., serum or plasma portion), and the solids area 806 connected to the target area 804 having a second average transverse dimension larger than the first average transverse dimension and a closed bottom end, wherein the solids area 806 contains substantially the solids portion 860 (e.g., the red blood cell portion). A probe 870 may be received in the target area 804 of the biological liquid collection vessel 800 and is adapted to aspirate at least a portion of the liquid portion 855 (e.g., serum or plasma) from the target area 804.

The probe 870 may be coupled to, or be part of, a liquid aspiration system 880 as shown in FIG. 8B, for example. The liquid aspiration system 880 may be part of a clinical analyzer or other instrument adapted to aspirate and/or dispense liquid biological fluids, reagents, and/or other liquids as part of testing the biological liquid.

Now referring to FIG. 8B, a representative embodiment of liquid aspiration system 880 is shown. The liquid aspiration system 880 includes at least one liquid source 882 fluidly coupled to a pump 884. The fluid coupling may be provided by any suitable passage, such as one or more liquid-carrying conduits, for example. The pump 884 is fluidly coupled to the probe 870. The fluid coupling on the output side of the pump 884 may be provided by any suitable passage, such as a flow-controllable passage comprising one or more conduits and one or more valves 886, for example. A suitable controller 888 may be provided to carry out the dispensing and/or aspirating by the pump 884.

In some embodiments, a liquid (e.g., purified water) may be provided from the liquid source 882 and may be used as a liquid backing to aspirate and dispense the liquid portion 855 (e.g., the serum or plasma portion) to and from the probe 870. For example, the purified water may be purified to a level that is suitable to be used for aspiration and/or dispensing in the testing of analytes or other substances in a biological liquid (e.g., plasma or serum portion).

Using the liquid as a backing liquid means that none or only a small amount of the backing liquid from the first liquid source 882 may be dispensed, but the backing liquid is present to draw in at least some of the liquid portion 855 thorough the probe 870 when aspirating, and push out the liquid portion 855 out of the probe 870 when dispensing. The aspiration and dispense operations may be accomplished by operation and control of the valves 886 and pump 884 by suitable control signals from the controller 888.

Accordingly, in each of the preceding embodiments, the target areas 104, 204, 304, 404, 504, 604, 704, and 804 are appropriately sized to accept a probe 870 therein. Because the target areas 104-804 are extended in length relative to conventional biological liquid collection vessels, more of the liquid portion 855 may be aspirated. Moreover, the placement of the probe 870 may be less exact, thus requiring less precise and possibly less expensive robotics. With reference to FIG. 8B, a length L of the target portions 104-804 may be between about 70 mm and about 20 mm in some embodiments. Other length values may be used. The first average transverse dimension (e.g., 104T) of the target area may be between about 2 mm and about 8 mm, or even about 3 mm to about 6 mm in some embodiments. The second average transverse dimension (e.g., 106T) of the solids area may be between about 2 mm and about 8 mm. Other average transverse dimensions may be used. In some embodiments, the first average transverse dimension (e.g., 104T) of the target area 104 may less than the second average transverse dimension (e.g., 106T) of the solids area 106. In yet other embodiments, a ratio of second average transverse dimension (e.g., 106T) divided by the first average transverse dimension (e.g., 104T) may be greater than about 1.2, for example.

Figure 9:
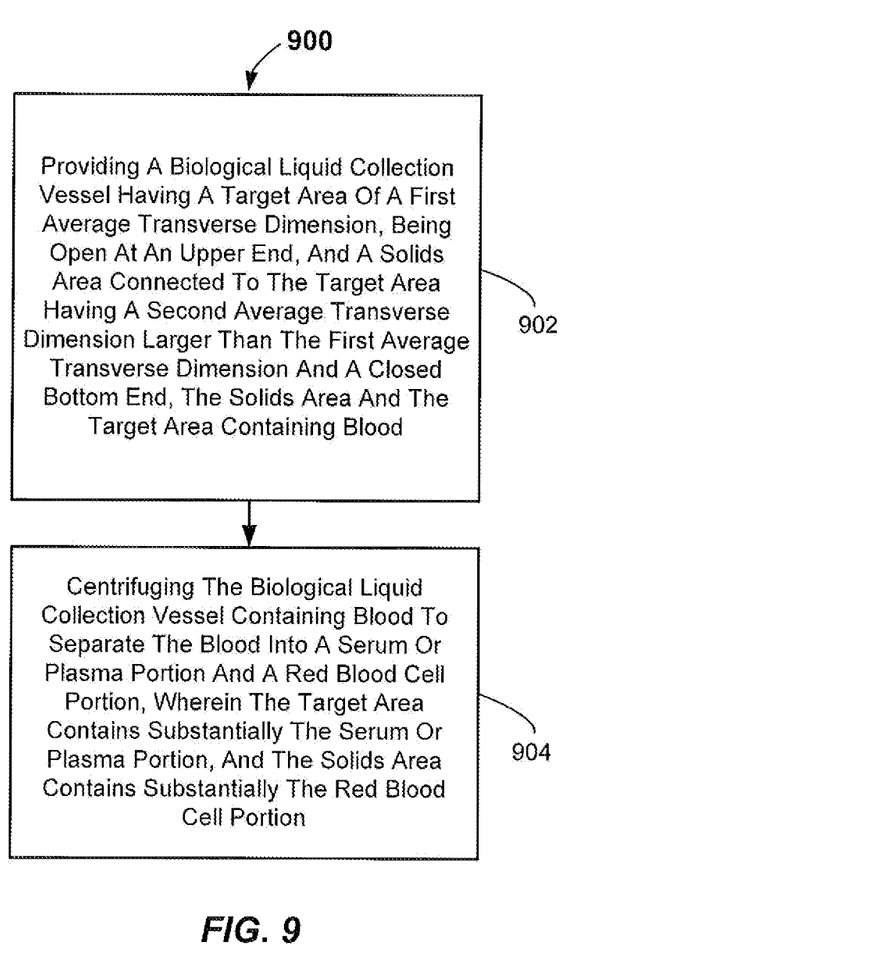
FIG. 9 is a flowchart illustrating a liquid centrifugation method according to embodiments.

According to another aspect, a liquid centrifugation method according to embodiments will now be described with reference to FIG. 9. The liquid centrifugation method 900 includes, in 902, providing a biological liquid collection vessel (e.g., 100, 200, 300, 400, 500, 600A-600E, 700) having a target area (e.g., 104, 204, 304, 404, 504, 704) of a first average transverse dimension, being open at an upper end, and a solids area (e.g., 106, 206, 306, 406, 506, 706) connected to the target area having a second average transverse dimension larger than the first average transverse dimension and a closed bottom end, the solids area and the target area containing blood, and, in 904, centrifuging the biological liquid collection vessel containing blood to separate the blood into a serum or plasma portion (e.g., 855) and a red blood cell portion (e.g., 860), wherein the target area contains substantially the serum or plasma portion, and the solids area contains substantially the red blood cell portion. In accordance with another aspect, as shown in FIG. 8A-8B, once the blood is centrifuged and separated into the liquid portion 855 (e.g., serum or plasma portion) and the solids portion 860 (e.g., red blood cell portion), a probe (e.g., 870) may be inserted into the target area of the biological liquid collection vessel containing substantially the liquid portion 855 (e.g., serum or plasma portion). The target area is appropriately sized to accept the probe (e.g., 870) and may include a taper thereon. Once inserted into the target area, aspiration of at least some of the liquid portion 855 (e.g., serum or plasma portion) may be carried out through the operation of the liquid aspiration system 880.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed, but, to the contrary, the intention is to cover all modifications, equivalents, and alternatives falling within the scope of the invention.

What is claimed is:

1. A biological liquid collection vessel, comprising:
a single-piece tube having an open end, a cap-receiving portion at the open end, a closed end, and a continuous inner wall extending from the open end to the closed end, the continuous inner wall adapted to be in contact with a biological liquid and to maintain a same shape, size, and volume capacity with and without the biological liquid in contact therewith, the continuous inner wall having an inner transverse dimension that continuously varies along at least half of a length of the continuous inner wall extending from the cap-receiving portion to the closed end, the inner transverse dimension having a minimum dimension located in between the open end and the closed end; and
an outer sleeve.

2. The biological liquid collection vessel of claim 1, wherein the biological liquid collection vessel is adapted to contain a biological liquid.

3. The biological liquid collection vessel of claim 1, wherein the single-piece tube has an outer dimension at a lower end between 10 mm and 20 mm.

4. The biological liquid collection vessel of claim 1, comprising:
a target area of a first average transverse dimension and adapted to contain a serum or plasma portion; and
a solids area connected to and adjacent the target area having a second average transverse dimension larger than the first average transverse dimension and adapted to contain a red blood cell portion.

5. The biological liquid collection vessel of claim 1, comprising a vacuum within a receiving cavity to allow collection of a biological liquid.

6. A biological liquid collection vessel, comprising:
an inner liner having an upper end that is open and a lower end that is closed, a continuous inner wall extending from the upper end to the lower end that maintains a same shape, size, and volume capacity with and without a serum, plasma, or red blood cell portion in contact therewith, and a target area and a solids area; and
an outer sleeve;
wherein:
the target area has a first average transverse dimension and is open at the upper end and is adapted to contain a serum or plasma portion, the continuous inner wall having an inner transverse dimension that continuously varies along its length in the target area; and
the solids area is connected to and adjacent the target area, has a second average transverse dimension larger than the first average transverse dimension, is closed at the lower end, and is adapted to contain a red blood cell portion.

7. The biological liquid collection vessel of claim 6, wherein the solids area and the target area are adapted to contain a total volume, and a volume of the solids area comprises 40% to 80% of the total volume.

8. The biological liquid collection vessel of claim 7, wherein the volume of the solids area comprises 50% to 70% of the total volume.

9. The biological liquid collection vessel of claim 6, wherein the solids area and the target area are adapted to contain a total volume, and a volume of the target area comprises 20% to 60% of the total volume.

10. The biological liquid collection vessel of claim 9, wherein the volume of the target area comprises 30% to 50% of the total volume.

11. The biological liquid collection vessel of claim 6, comprising an inner taper formed along greater than half a length of the target area, the inner taper having a wider dimension adjacent to the upper end.

12. The biological liquid collection vessel of claim 11, wherein the inner taper comprises a taper angle of between about 0.25 and about 30 degrees.

13. The biological liquid collection vessel of claim 11, wherein the inner taper comprises a taper angle of between about 0.25 and about 15 degrees.

14. The biological liquid collection vessel of claim 6, comprising a reverse taper formed along an upper portion of the solids area wherein the reverse taper has a minimum dimension adjacent to the target area.

15. The biological liquid collection vessel of claim 6, comprising a cap-receiving portion.

16. The biological liquid collection vessel of claim 6, comprising a total volume capacity of the solids area plus the target area of less than or equal to 3 mL.

17. The biological liquid collection vessel of claim 16, comprising a total volume capacity of the solids area plus the target area of less than or equal to 2 mL.

18. The biological liquid collection vessel of claim 16, comprising a total volume capacity of the solids area plus the target area of less than or equal to 1 mL.

19. The biological liquid collection vessel of claim 6, wherein the outer sleeve comprises a first volume capacity V1, the inner liner comprises a second volume capacity V2, and V2 is less than V1.

20. The biological liquid collection vessel of claim 19, wherein the outer sleeve comprises a first volume capacity V1, the inner liner comprises a second volume capacity V2, and a ratio of V2/V1 is between about 0.167 to about 0.8.

21. The biological liquid collection vessel of claim 6, comprising volume capacities of both of the target area and the solids area being sized so that a centrifuged biological liquid having a red blood cell portion and a serum or plasma portion, when contained in the biological liquid collection vessel, the red blood cell portion is substantially contained in the solids area, and the serum or plasma portion is substantially contained in the target area.

22. The biological liquid collection vessel of claim 6, containing a centrifuged biological liquid having a red blood cell portion and a serum or plasma portion, comprising the red blood cell portion being substantially contained in the solids area, and the serum or plasma portion being substantially contained in the target area.

23. A biological liquid collection vessel containing a centrifuged biological liquid, comprising:
an inner liner having an upper end that is open and a lower end that is closed, a single-piece, continuous inner wall extending from the upper end to the lower end that maintains a same shape, size, and volume capacity with and without the centrifuged biological liquid in contact therewith, and a target area and a solids area; and
an outer sleeve;
wherein:
the target area is open at the upper end and has a continuously varying inner transverse dimension, the solids area is connected to and adjacent the target area and closed at the lower end, and volume capacities of both of the target area and the solids area are positioned so that a red blood cell portion of the centrifuged biological liquid is substantially contained in the solids area, and a serum or plasma portion of the centrifuged biological liquid is substantially contained in the target area.

24. A liquid centrifugation method, comprising:

providing a biological liquid collection vessel having an inner liner comprising an open upper end, a closed bottom end, a cap-receiving portion having a first length extending from the open upper end, a target area of a first average transverse dimension-having a second length longer than the first length and located proximate the open upper end, and a solids area connected to and adjacent the target area and having a second average transverse dimension larger than the first average transverse dimension and extending to the closed bottom end, the solids area and the target area containing blood, the biological liquid collection vessel also having a continuous inner wall of constant thickness extending from the open upper end to the closed bottom end that maintains a same shape, size, and volume capacity with and without the blood in contact therewith, and an outer sleeve; and centrifuging the biological liquid collection vessel containing blood to separate the blood into a serum or plasma portion and a red blood cell portion, wherein the target area contains substantially the serum or plasma portion, and the solids area contains substantially the red blood cell portion.

25. The method of claim 24, comprising:

inserting a probe into the target area of the biological liquid collection vessel containing substantially the serum or plasma portion.

26. The method of claim 25, comprising:

aspirating with the probe inserted into the target area, at least some of the serum or plasma portion.

27. A biological liquid collection vessel, comprising:

an inner liner comprising:
- an open upper end;
- a closed bottom end;
- a cap-receiving portion proximate the open upper end;
- a target area having a constant first transverse dimension located proximate the cap-receiving portion; and
- a solids area connected to and adjacent the target area, having a second transverse dimension larger than the constant first transverse dimension, and extending to the closed bottom end; and
- a continuous, single-piece inner wall of a constant thickness extending from the open upper end to the closed bottom end that maintains a same shape, size, and volume capacity with and without serum or plasma or red blood cells in contact therewith; and an outer sleeve.

* * * * *